(12) United States Patent
Thomas

(10) Patent No.: US 9,867,555 B1
(45) Date of Patent: Jan. 16, 2018

(54) SHOE PLATFORM MEASUREMENT SCALES

(71) Applicant: John A. Thomas, Laurelton, NY (US)

(72) Inventor: John A. Thomas, Laurelton, NY (US)

(*) Notice: Subject to any disclaimer, the term of this patent is extended or adjusted under 35 U.S.C. 154(b) by 0 days.

(21) Appl. No.: 15/415,190

(22) Filed: Jan. 25, 2017

(51) Int. Cl.
*A61B 5/103* (2006.01)
*A61B 5/107* (2006.01)
*G01C 9/28* (2006.01)

(52) U.S. Cl.
CPC .......... *A61B 5/1072* (2013.01); *A61B 5/1074* (2013.01); *G01C 9/28* (2013.01)

(58) Field of Classification Search
CPC ..... A61B 5/1036; A61B 5/1038; A61B 5/107; A61B 5/1072; A61B 5/1074; A61H 2230/70; A61H 1/005; G01C 9/28
USPC .................. 33/381; 600/587, 592, 594, 595; 601/27–31, 98
See application file for complete search history.

(56) References Cited

U.S. PATENT DOCUMENTS

| | | | |
|---|---|---|---|
| 2,096,615 A * | 10/1937 | MacDonald | A43D 1/02 33/2 R |
| 5,088,504 A | 2/1992 | Benesh et al. | |
| 5,406,719 A | 4/1995 | Potter | |
| 5,437,110 A | 8/1995 | Goldston et al. | |
| 5,490,518 A * | 2/1996 | Russo | A61B 5/107 600/587 |
| 5,813,142 A | 9/1998 | Demon | |
| 5,979,067 A * | 11/1999 | Waters | A61B 5/1036 33/512 |
| 6,761,666 B2 * | 7/2004 | Chou | A63B 22/0056 482/52 |
| 6,931,746 B2 | 8/2005 | Pourmanafzadeh | |
| 9,295,876 B2 * | 3/2016 | Singh | A63B 23/085 |
| 9,302,153 B2 * | 4/2016 | Harwin | A63B 26/003 |
| 9,737,237 B2 * | 8/2017 | Marovets | A61B 5/1072 |
| 2004/0044296 A1 | 3/2004 | Linton | |
| 2005/0055848 A1 | 3/2005 | Miller et al. | |

* cited by examiner

Primary Examiner — William V Gilbert (57) ABSTRACT

A therapeutic measuring device that determines a difference in length between a pair of legs of a user. The therapeutic measuring device includes a stationary platform and a movable platform. The stationary platform has one leg of the user stand thereon. The movable platform has the other leg of the user stand thereon. The movable platform is moved vertically until the other leg of the user standing thereon aligns with the one leg of the user standing on the stationary platform, with an amount of elevation of the movable platform determining the difference in the length between the pair of legs of the user.

91 Claims, 2 Drawing Sheets

SHOE PLATFORM MEASUREMENT SCALES

BACKGROUND OF THE INVENTION

Field of the Invention

The present invention relates to a measuring device, and more particularly, a therapeutic measuring device for determining a difference in length between a pair of legs of a user.

Description of the Prior Art

Numerous innovations for therapeutic shoes and leg length measuring devices have been provided in the prior art that will be described. Even though these innovations may be suitable for the specific individual purposes to which they address, however, they differ from the present invention.

A FIRST EXAMPLE, U.S. Pat. No. 5,406,719, Published/Issued on Apr. 18, 1995, to Potter teaches a cushioning element for use in a shoe. The cushioning element includes four fluid-filled support chambers that are compressible but not collapsible, and which are disposed at different locations throughout the midsole of the shoe. The element also includes four variable-volume and fluid-reservoir chambers that are collapsible to reduce the volume thereof. The reservoir chambers are controllably linked in fluid communication with the support chambers so as to be selectively in full communication with, or isolated from, the support chambers. By selectively isolating one or more of the reservoir chambers from one or more of the support chambers, and collapsing the isolated chamber, fluid may be moved from one support chamber to another at a different location, thereby increasing the stiffness of the midsole at a selected location.

A SECOND EXAMPLE, U.S. Pat. No. 5,437,110, Published/Issued on Aug. 1, 1995, to Goldston, et al. teaches an adjustable shoe heel spring and stabilizer device for providing the wearer of a shoe the ability to adjust the energy absorption and return characteristics of the shoe to suit their particular needs. An operable adjustment device is located on an exterior surface of the shoe. The wearer operates the adjustment device to selectively position a fulcrum at a desired location relative to upper and lower members of a spring mechanism disposed within the mid-sole of the shoe. The position of the fulcrum defines the energy absorption and return characteristics for the shoe. An indicator is provided for displaying to the wearer the relative position of the fulcrum, and hence the energy absorption and return setting for the shoe.

A THIRD EXAMPLE, U.S. Pat. No. 5,813,142, Published/Issued on Sep. 29, 1998, to Demon teaches a shoe having a adjustable cushion sole with fluid bladders disposed therein. Each fluid bladder has an associated pressure sensing device that measures the pressure exerted by the user's foot on the fluid bladder. As the pressure increases over a threshold, a control system partially opens a fluid valve to allow fluid to escape from the fluid bladder. The release of fluid from the fluid bladders reduces the impact of the user's foot with the traveling surface.

A FOURTH EXAMPLE, U.S. Patent Office Document No. 2005/0055848, Published/Issued on Mar. 17, 2005, to Miller, et al. teaches an expandable shoe including an outer shell and an adjustable inner assembly within the outer shell. The inner assembly includes a first sole portion, a second sole portion, and a screw drive. The screw drive has a screw passing through a screw insert mounted to one of the first and second sole portions and a screw-receiving portion attached to the other of the first and second sole portions, so that turning the screw causes the sole portions to move relative to one another, thereby adjusting a dimension of the shoe. The shoe includes a manually operable control to turn the screw without a need for tools. The control is operable between a first position in which the control resists movement around an axis defined by the screw and a second position in which the control can be used to turn the screw to adjust a dimension of the footwear.

A FIFTH EXAMPLE, U.S. Pat. No. 5,088,504, Published/Issued on Feb. 18, 1992, to Benesh, et al. teaches a machine that measures and records in terms of the orientation planes of motion, the presence of, the location of, and the severity of the postural distortion-stress effects of C-1 subluxations on the human body, making it possible thereby statistical analyses between C-1 misalignments (determined by X-ray analysis) and postural distortion-stress effects on the skeletal framework as directly resulted from the misalignment interferences of C-1 on the nervous system and its normal functioning. The machine can demonstrate the postural distortion-stress effects of C-1 subluxation on the spine by checking the malpositional relationships of upper thoracic vertebral segments and pelvis prior to, and subsequent to, C-1 correction, indicating thereby the corrections obtainable throughout the spine, and thus reducing a need for repeated applications of X-radiation to the patient. The machine has movable elements that provide indications of corrections or displacement, and has a pair of weight sensitive platforms with horizontally adjustable pads (foot guides). The platforms are coupled to force transducers that indicate apparatus for measuring the portion of total body weight that is supported by each of the patient's feet. The pads are individually or simultaneously adjustable toward and away from each other to properly space the feet relative to the ilii.

A SIXTH EXAMPLE, U.S. Pat. No. 5,490,518, Published/Issued on Feb. 13, 1996, to Russo, et al. teaches a leg length inequality measuring device to quantitatively determine one of the signs of postural imbalance. The device is for use by chiropractic practionters. Both legs are usually of the same length, but when the skeleton of a patient is out of alignment, an appearance of differing leg lengths is presented, and the cause and treatment are decided by determining accurately if there is a difference in leg length. A device for this purpose is in the form of a solid rectangle with stepped or V-shaped edge slots arranged with a pair of these slots running across the top surface thereof, and the other slot running perpendicular to the two cross-slots and along the length of the bottom face of the item. The two cross-slots are for accommodating sliding measuring slabs to various positions in order to determine the difference in leg length measurement for each leg as the patient lies on his or her belly with heels against the slabs. The lengthwise slab for motion in the lengthwise slot is to accommodate, for instance, bulging thighs of the patient. Set screws are used to fix, when needed, the motion of the sliding slabs.

A SEVENTH EXAMPLE, U.S. Pat. No. 6,931,746, Published/Issued on Aug. 23, 2005, to Pourmanafzadeh teaches an apparatus and method for determining difference in leg height of a standing patient by making a first measurement while the patient stands on a first foot, making a second measurement while the patient stands on a second foot, and determining the vertical distance between the first measurement and the second measurement. One embodiment incorporates a scale with a sliding wide measurement plate to measure the top of the head. Another embodiment provides a wide height measurement plate to retrofit existing height scales, and a fabrication kit for making that plate. In another embodiment, the patient wears an apron with reference markings that may be observed through a movable reference grid. The observation may be manual or optically with a camera or scanner.

AN EIGHTH EXAMPLE, U.S. Patent Office Document No. 2004/0044296, Published/Issued on Mar. 4, 2004, to Linton teaches an apparatus for measuring body symmetry. The apparatus includes a pair of supports, a level, and apparatus for determining support displacement. The supports position the apparatus on left and right body points that are generally symmetrical about a patient's spinal column. The level indicates whether the first support is higher or lower than the second support when placed upon the left and right body points thereby identifying that the body points are not actually symmetrical. The means for determining support displacement determine the displacement of one support relative to the other in a vertical direction when one body point is higher or lower than the other body point. The apparatus is utilized to determine hip or shoulder symmetry and displacement.

It is apparent now that numerous innovations for therapeutic shoes and leg length measuring devices have been provided in the prior art that adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide a shoe platform measurement scales that avoids the disadvantages of the prior art.

ANOTHER OBJECT of the present invention is to provide a shoe platform measurement scales that is simple and inexpensive to manufacture.

STILL ANOTHER OBJECT of the present invention is to provide a shoe platform measurement scales that is simple to use.

BRIEFLY STATED, STILL YET ANOTHER OBJECT of the present invention is to provide a therapeutic measuring device that determines a difference in length between a pair of legs of a user. The therapeutic measuring device includes a stationary platform and a movable platform. The stationary platform has one leg of the user stand thereon. The movable platform has the other leg of the user stand thereon. The movable platform is moved vertically until the other leg of the user standing thereon aligns with the one leg of the user standing on the stationary platform, with an amount of elevation of the movable platform determining the difference in the length between the pair of legs of the user.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWINGS

The figures of the drawings are briefly described as follows.

A MARSHALING OF REFERENCE NUMERALS UTILIZED IN THE DRAWINGS

Introductory

10 therapeutic measuring device of embodiments of present invention for determining difference in length between pair of legs of user 14
12 pair of legs of user 14
14 user Overall Configuration of Therapeutic Measuring Device 10

16 stationary platform for having one leg 12 of user 14 stand thereon
18 movable platform for having other leg 12 of user 14 stand thereon
20 pair of anti-torsion bars Specific Configuration of Stationary Platform 16

22 outer side of stationary platform 16
24 inner side of stationary platform 16
26 front side of stationary platform 16
28 rear side of stationary platform 16
30 top side of stationary platform 16
32 bottom side of stationary platform 16
34 front level of stationary platform 16
36 rear level of stationary platform 16
38 outer level of stationary platform 16
40 inner level of stationary platform 16

Specific Configuration of Movable Platform 18

42 stationary portion of movable platform 18
44 movable portion of movable platform 18

Specific Configuration of Stationary Portion 42 of Movable Platform 18

46 outer side of stationary portion 42 of movable platform 18
48 inner side of stationary portion 42 of movable platform 18
50 front side of stationary portion 42 of movable platform 18
52 rear side of stationary portion 42 of movable platform 18
54 top side of stationary portion 42 of movable platform 18
56 bottom side of stationary portion 42 of movable platform 18
57 height of stationary portion 42 of movable platform 18
58 front level of stationary portion 42 of movable platform 18
60 rear level of stationary portion 42 of movable platform 18

62 outer level of stationary portion 42 of movable platform 18
64 inner level of stationary portion 42 of movable platform 18
65 level support surface
66 screw jack assembly
68 trough of top side 54 of stationary portion 42 of movable platform 18
70 outer side of trough 68 of stationary portion 42 of movable platform 18
72 inner side of trough 68 of stationary portion 42 of movable platform 18
74 front side of trough 68 of stationary portion 42 of movable platform 18
76 rear side of trough 68 of stationary portion 42 of movable platform 18
78 top side of trough 68 of stationary portion 42 of movable platform 18
80 bottom side of trough 68 of stationary portion 42 of movable platform 18
81 height of trough 68 of stationary portion 42 of movable platform 18

Specific Configuration of Movable Portion 44 of Movable Platform 18

82 outer side of movable portion 44 of movable platform 18
84 inner side of movable portion 44 of movable platform 18
86 front side of movable portion 44 of movable platform 18
88 rear side of movable portion 44 of movable platform 18
90 top side of movable portion 44 of movable platform 18
92 bottom side of movable portion 44 of movable platform 18
94 front level of movable portion 44 of movable platform 18
96 rear level of movable portion 44 of movable platform 18
98 outer level of movable portion 44 of movable platform 18
100 inner level of movable portion 44 of movable platform 18
102 measuring scale of outer side 82 of movable portion 44 of movable platform 18 for indicating difference in length between pair of legs 12 of user 14

Specific Configuration of Screw Jack Assembly 66

104 vertical portion of screw jack assembly 66
106 horizontal portion of screw jack assembly 66
108 bore of screw jack assembly 66
110 Allen key of screw jack assembly 66

DETAILED DESCRIPTION OF THE PREFERRED EMBODIMENT

Introductory

Figure 4:
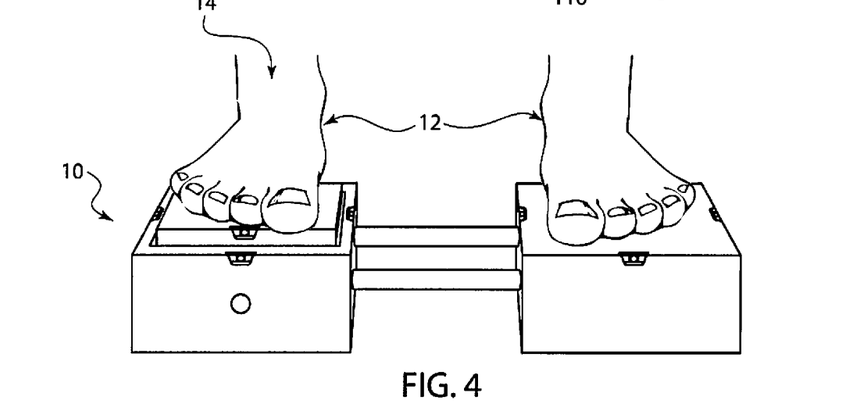
FIG. 4 is a diagrammatic front-top perspective view of the shoe platform measurement scales illustrated with the feet of a person standing thereon so that an appropriate measurement can be made.

Referring now to the figures, in which like numerals indicate like parts, and particularly to FIG. 4, the therapeutic measuring device of the embodiments of the present invention is shown generally at 10 for determining a difference in length between a pair of legs 12 of a user 14.

Overall Configuration of the Therapeutic Measuring Device 10

Figure 1:
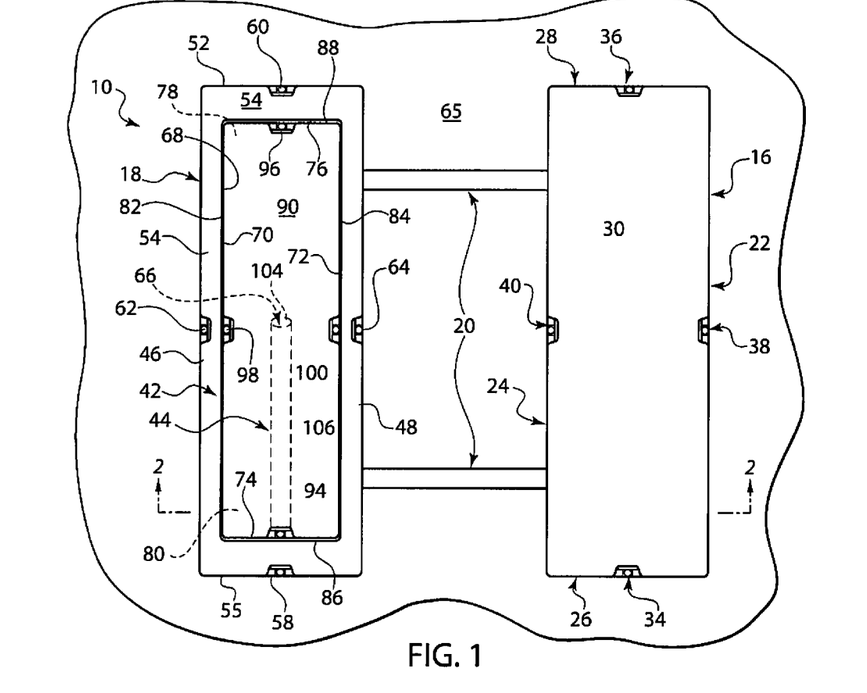
FIG. 1 is a diagrammatic top plan view of a preferred embodiment of the shoe platform measurement scales.
Figure 2:
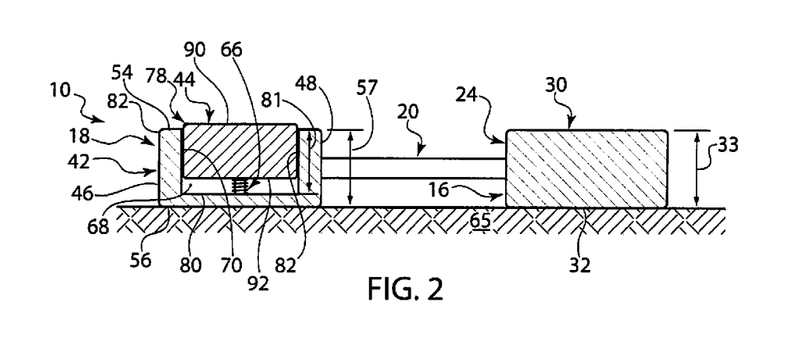
FIG. 2 is a cross sectional view taken on line 2-2 of FIG. 1.

The overall configuration of the therapeutic measuring device 10 can best be seen in FIGS. 1 and 2, and as such, will be discussed with reference thereto.

The therapeutic measuring device 10 comprises a stationary platform 16 and a movable platform 18. The stationary platform 16 is for having one leg 12 of the user 14 stand thereon. The movable platform 18 is for having the other leg 12 of the user 14 stand thereon. The movable platform 18 is moved vertically until the other leg 12 of the user 14 standing thereon aligns with the one leg 12 of the user 14 standing on the stationary platform 16, with an amount of elevation of the movable platform 18 determining the difference in the length between the pair of legs 12 of the user 14.

The therapeutic measuring device 10 further comprises a pair of anti-torsion bars 20.

The pair of anti-torsion bars 20 are parallel to each other and extend from the stationary platform 16 to the movable platform 18 so as to maintain the stationary platform 16 parallel to the movable platform 18 and prevent rotation therebetween.

Specific Configuration of the Stationary Platform 16

The specific configuration of the stationary platform 16 can best be seen in FIGS. 1 and 2, and as such, will be discussed with reference thereto.

The stationary platform 16 is parallelepiped-shaped, and as such, has an outer side 22, an inner side 24, a front side 26, a rear side 28, a top side 30, a bottom side 32, and a height 33.

The top side 30 of the stationary platform 16 is for having the one leg 12 of the user 14 stand thereon.

The stationary platform 16 further has a front level 34, a rear level 36, an outer level 38, and an inner level 40, which are for use in assuring that the stationary platform 16 is perfectly level initially when viewed from any viewing point.

For novices in the field of levels, Applicant Thomas will present a basic explanation regarding "levels."

A spirit level, bubble level, or simply a level is an instrument designed to indicate whether a surface is horizontal (level) or vertical (plumb). Different types of spirit levels may be used by carpenters, stonemasons, bricklayers, other building trades workers, surveyors, millwrights, and other metalworkers, and in some photographic or videographic work.

Early spirit levels had very slightly curved glass vials with constant inner diameter at each viewing point. These vials are incompletely filled with a liquid, usually a colored spirit or alcohol, leaving a bubble in the tube. They have a slight upward curve, so that the bubble naturally rests in the center, the highest point. At slight inclinations, the bubble travels away from the marked center position. Where a spirit level must also be usable upside-down or on its side, the curved constant-diameter tube is replaced by an uncurved barrel-shaped tube with a slightly larger diameter in its middle.

Alcohols, such as, ethanol are often used rather than water. Alcohols have low viscosity and surface tension, which allows the bubble to travel the tube quickly and settle accurately with minimal interference with the glass surface. Alcohols also have a much wider liquid temperature range, and won't break the vial as water could due to ice expansion. A colorant, such as, fluorescein, typically yellow or green, may be added to increase the visibility of the bubble.

An extension of the spirit level is the bull's eye level. A bull's eye level is a circular and flat-bottomed device having the liquid under a slightly convex glass face with a circle at the center. It serves to level a surface across a plane, while the tubular level only does so in the direction of the tube.

The front level 34 of the stationary platform 16 is disposed where the top side 30 of the stationary platform 16 meets the front side 26 of the stationary platform 16, midway therealong.

The rear level 36 of the stationary platform 16 is disposed where the top side 30 of the stationary platform 16 meets the rear side 28 of the stationary platform 16, midway therealong.

The outer level 38 of the stationary platform 16 is disposed where the top side 30 of the stationary platform 16 meets the outer side 22 of the stationary platform 16, midway therealong.

The inner level 40 of the stationary platform 16 is disposed where the top side 30 of the stationary platform 16 meets the inner side 24 of the stationary platform 16, midway therealong.

Specific Configuration of the Movable Platform 18

The specific configuration of the movable platform 18 can best be seen in FIGS. 1 and 2, and as such, will be discussed with reference thereto.

The movable platform 18 includes a stationary portion 42 and a movable portion 44. The movable portion 44 of the movable platform 18 moves relative to the stationary portion 42 of the movable platform 18.

Specific Configuration of the Stationary Portion 42 of the Movable Platform 18

The stationary portion 42 of the movable platform 18 is parallelepiped-shaped, and as such, has an outer side 46, an inner side 48, a front side 50, a rear side 52, a top side 54, a bottom side 56, and a height 57.

The stationary portion 42 of the movable platform 18 further has a front level 58, a rear level 60, an outer level 62, and an inner level 64, which are for use in assuring that the stationary portion 42 of the movable platform 18 is perfectly level initially when viewed from any viewing point.

The front level 58 of the stationary portion 42 of the movable platform 18 is disposed where the top side 54 of the stationary portion 42 of the movable platform 18 meets the front side 50 of the stationary portion 42 of the movable platform 18, midway therealong.

The rear level 60 of the stationary portion 42 of the movable platform 18 is disposed where the top side 54 of the stationary portion 42 of the movable platform 18 meets the rear side 52 of the stationary portion 42 of the movable platform 18, midway therealong.

The outer level 62 of the stationary portion 42 of the movable platform 18 is disposed where the top side 54 of the stationary portion 42 of the movable platform 18 meets the outer side 46 of the stationary portion 42 of the movable platform 18, midway therealong.

The inner level 64 of the stationary portion 42 of the movable platform 18 is disposed where the top side 54 of the stationary portion 42 of the movable platform 18 meets the inner side 48 of the stationary portion 42 of the movable platform 18, midway therealong.

The height 57 of the stationary portion 42 of the movable platform 18 is equal to the height 33 of the stationary platform 16 when both are placed upon a level support surface 65.

The stationary portion 42 of the movable platform 18 contains a screw jack assembly 66.

The top side 54 of the stationary portion 42 of the movable platform 18 further contains a trough 68.

The trough 68 of the stationary portion 42 of the movable platform 18 is parallelepiped-shaped, and as such, has an outer side 70, an inner side 72, a front side 74, a rear side 76, a top side 78, a bottom side 80, and a height 81.

The trough 68 of the stationary portion 42 of the movable platform 18 snugly receives the movable portion 44 of the movable platform 18 so as to allow the movable portion 44 of the movable platform 18 to move only directly vertically, without twisting, in the trough 68 of the stationary portion 42 of the movable platform 18 for maintaining the movable portion 44 of the movable platform 18 consistently level.

The outer side 70 of the trough 68 of the stationary portion 42 of the movable platform 18 is parallel to, and inward of, the outer side 46 of the stationary portion 42 of the movable platform 18.

The inner side 72 of the trough 68 of the stationary portion 42 of the movable platform 18 is parallel to, and inward of, the inner side 48 of the stationary portion 42 of the movable platform 18.

The front side 74 of the trough 68 of the stationary portion 42 of the movable platform 18 is parallel to, and inward of, the front side 50 of the stationary portion 42 of the movable platform 18.

The rear side 76 of the trough 68 of the stationary portion 42 of the movable platform 18 is parallel to, and inward of, the rear side 52 of the stationary portion 42 of the movable platform 18.

The top side 78 of the trough 68 of the stationary portion 42 of the movable platform 18 is open.

The bottom side 80 of the trough 68 of the stationary portion 42 of the movable platform 18 is parallel to, and upwards of, the bottom side 56 of the stationary portion 42 of the movable platform 18.

Specific Configuration of the Movable Portion 44 of the Movable Platform 18

The movable portion 44 of the movable platform 18 is parallelepiped-shaped, and as such, has an outer side 82, an inner side 84, a front side 86, a rear side 88, a top side 90, and a bottom side 92.

The outer side 82 of the movable portion 44 of the movable platform 18 is parallel to, and inward of, the outer side 46 of the stationary portion 42 of the movable platform 18, and is substantially coplanar with the outer side 70 of the trough 68 of the stationary portion 42 of the movable platform 18.

The inner side 84 of the movable portion 44 of the movable platform 18 is parallel to, and inward of, the inner side 48 of the stationary portion 42 of the movable platform 18, and is substantially coplanar with the inner side 72 of the trough 68 of the stationary portion 42 of the movable platform 18.

The front side 74 of the movable portion 44 of the movable platform 18 is parallel to, and inward of, the front side 50 of the stationary portion 42 of the movable platform 18, and is substantially coplanar with the front side 74 of the trough 68 of the stationary portion 42 of the movable platform 18.

The rear side 76 of the movable portion 44 of the movable platform 18 is parallel to, and inward of, the rear side 52 of the stationary portion 42 of the movable platform 18, and is substantially coplanar with the rear side 76 of the trough 68 of the stationary portion 42 of the movable platform 18.

The bottom side 92 of the movable portion 44 of the movable platform 18 is parallel to, and upwards of, the bottom side 56 of the stationary portion 42 of the movable platform 18.

The movable portion 44 of the movable platform 18 further has a front level 94, a rear level 96, an outer level 98, and an inner level 100, which are for use in assuring that the movable portion 44 of the movable platform 18 is perfectly level initially when viewed from any viewing point.

The front level 94 of the movable portion 44 of the movable platform 18 is disposed where the top side 90 of the movable portion 44 of the movable platform 18 meets the front side 86 of the movable portion 44 of the movable platform 18, midway therealong.

The rear level 96 of the movable portion 44 of the movable platform 18 is disposed where the top side 90 of the movable portion 44 of the movable platform 18 meets the rear side 76 of the movable portion 44 of the movable platform 18, midway therealong.

The outer level 98 of the movable portion 44 of the movable platform 18 is disposed where the top side 90 of the movable portion 44 of the movable platform 18 meets the outer side 82 of the movable portion 44 of the movable platform 18, midway therealong.

The inner level 94 of the movable portion 44 of the movable platform 18 is disposed where the top side 90 of the movable portion 44 of the movable platform 18 meets the inner side 84 of the movable portion 44 of the movable platform 18, midway therealong.

Figures 3, 5:
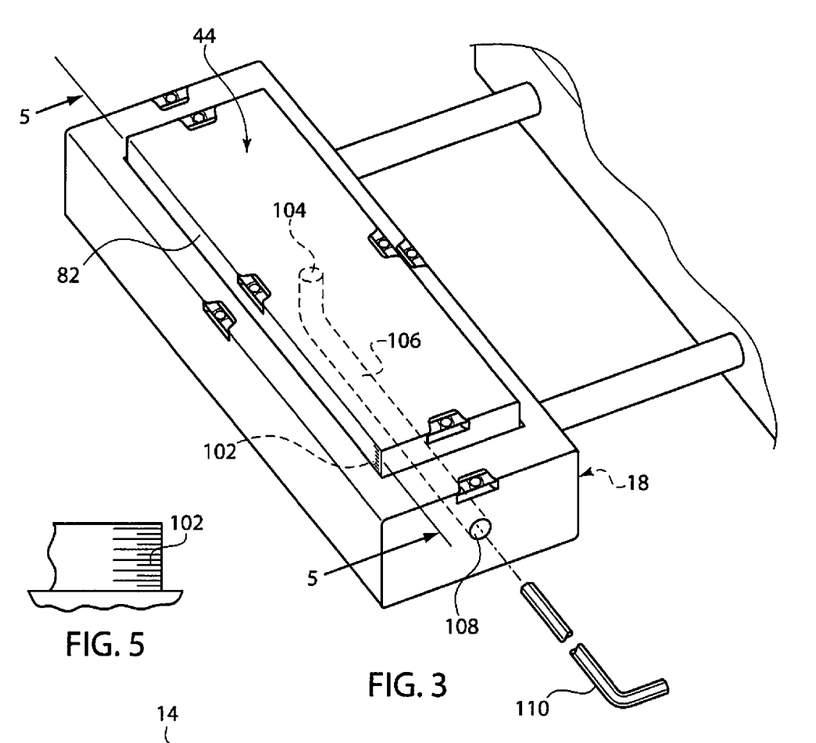
FIG. 3 is a diagrammatic perspective view, with parts broken away, of a portion of the shoe platform measurement scales.
FIG. 5 is an enlarged diagrammatic side elevational view, taken on line 5-5 in FIG. 3, of the scale system.

As shown in FIGS. 3 and 5, the outer side 82 of the movable portion 44 of the movable platform 18 has a measuring scale 102 therealong for viewing.

The measuring scale 102 of the outer side 82 of the movable portion 44 of the movable platform 18 determines how far the movable portion 44 of the movable platform 18 has been raised out of the stationary portion 42 of the movable platform 18, which in turn is for indicating the difference in length between the pair of legs 12 of the user 14.

Specific Configuration of the Screw Jack Assembly 66

The specific configuration of the screw jack assembly 66 is shown diagrammatically since a number of different configurations can be used. The specific configuration of the screw jack assembly 66 can best be seen in FIGS. 1-3, and as such, will be discussed with reference thereto.

An advantage of jackscrews over some other types of jack is that they are self-locking, which means when the rotational force on the screw is removed, it will remain motionless where it was left and will not rotate backwards, regardless of how much load it is supporting. This makes them inherently safer than hydraulic jacks, for example, that will move backwards under load if the force on the hydraulic actuator is accidentally released.

The screw jack assembly 66 has a vertical portion 104 and a horizontal portion 106.

The vertical portion 104 of the screw jack assembly 66 extends upwardly and centrally from the bottom side 80 of the trough 68 of the stationary portion 42 of the movable platform 18 to the bottom side 92 of the movable portion 44 of the movable platform 18, at the center of gravity of the movable portion 44 of the movable platform 18.

The horizontal portion 106 of the screw jack assembly 66 extends operatively from the vertical portion 104 of the screw jack assembly 66, through the stationary portion 42 of the movable platform 18, and terminates at the front side 50 of the stationary portion 42 of the movable platform 18 as a bore 108.

The bore 108 of the horizontal portion 106 of the screw jack assembly 66 is for receiving an Allen key 110, which when rotated, rotates the horizontal portion 106 of the screw jack assembly 66, which in turn rotates the vertical portion 104 of the screw jack assembly 66, causing the movable portion 44 of the movable platform 18 to raise revealing a point on the measuring scale 102 of the outer side 82 of the movable portion 44 of the movable platform 18, and thereby disclosing the difference in length of the pair of legs 12 of the user 14.

Impressions

It will be understood that each of the elements described above, or two or more together, may also find a useful application in other types of constructions differing from the types described above.

While the invention has been illustrated and described as embodiments of a shoe platform measurement scales, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A therapeutic measuring device for determining a difference in length between a pair of legs of a user, comprising:
   a) a stationary platform; and
   b) a movable platform;
   c) a pair of anti-torsion bars parallel to each other and extending from one side of said stationary platform to an adjacent side of said movable platform so as to maintain said stationary platform parallel to said movable platform and prevent rotation therebetween;
   d) a screw jack assembly connected to said movable platform;
   wherein said stationary platform is configured to have one leg of the user stand thereon and define a first elevation; wherein said movable platform is configured to have the other leg of the user stand thereon; and wherein said movable platform is configured to move vertically and define a second elevation relative to said first elevation when said user stands on said movable platform to align said legs, where a difference between said first elevation and said second elevation defines the difference in the length between said pair of legs of said user.

2. The therapeutic measuring device of claim 1, wherein said stationary platform has an outer side.

3. The therapeutic measuring device of claim 2, wherein said stationary platform has an inner side.

4. The therapeutic measuring device of claim 3, wherein said stationary platform has a front side.

5. The therapeutic measuring device of claim 4, wherein said stationary platform has a rear side.

6. The therapeutic measuring device of claim 5, wherein said stationary platform has a top side.

7. The therapeutic measuring device of claim 6, wherein said stationary platform has a front level.

8. The therapeutic measuring device of claim 7, wherein said front level of said stationary platform is disposed where said top side of said stationary platform meets said front side of said stationary platform, midway therealong.

9. The therapeutic measuring device of claim 6, wherein said stationary platform has a rear level.

10. The therapeutic measuring device of claim 9, wherein said rear level of said stationary platform is disposed where said top side of said stationary platform meets said rear side of said stationary platform, midway therealong.

11. The therapeutic measuring device of claim 6, wherein said stationary platform has an outer level.

12. The therapeutic measuring device of claim 11, wherein said outer level of said stationary platform is disposed where said top side of said stationary platform meets said outer side of said stationary platform, midway therealong.

13. The therapeutic measuring device of claim 6, wherein said stationary platform has an inner level.

14. The therapeutic measuring device of claim 13, wherein said inner level of said stationary platform is disposed where said top side of said stationary platform meets said inner side of said stationary platform, midway therealong.

15. The therapeutic measuring device of claim 1, wherein said stationary platform has a bottom side.

16. The therapeutic measuring device of claim 1, wherein said stationary platform has a height.

17. The therapeutic measuring device of claim 16, wherein said movable platform includes a stationary portion.

18. The therapeutic measuring device of claim 17, wherein said stationary portion of said movable platform is parallelepiped-shaped.

19. The therapeutic measuring device of claim 17, wherein said movable platform includes a movable portion.

20. The therapeutic measuring device of claim 19, wherein said movable portion of said movable platform is parallelepiped-shaped.

21. The therapeutic measuring device of claim 19, wherein said movable portion of said movable platform moves relative to said stationary portion of said movable platform.

22. The therapeutic measuring device of claim 19, wherein said stationary portion of said movable platform has an outer side.

23. The therapeutic measuring device of claim 22, wherein said stationary portion of said movable platform has an inner side.

24. The therapeutic measuring device of claim 23, wherein said stationary portion of said movable platform has a front side.

25. The therapeutic measuring device of claim 24, wherein said stationary portion of said movable platform has a rear side.

26. The therapeutic measuring device of claim 25, wherein said stationary portion of said movable platform has a top side.

27. The therapeutic measuring device of claim 26, wherein said stationary portion of said movable platform has a front level.

28. The therapeutic measuring device of claim 27, wherein said front level of said stationary portion of said movable platform is disposed where said top side of said stationary portion of said movable platform meets said front side of said stationary portion of said movable platform, midway therealong.

29. The therapeutic measuring device of claim 26, wherein said stationary portion of said movable platform has a rear level.

30. The therapeutic measuring device of claim 29, wherein said rear level of said stationary portion of said movable platform is disposed where said top side of said stationary portion of said movable platform meets said rear side of said stationary portion of said movable platform, midway therealong.

31. The therapeutic measuring device of claim 26, wherein said stationary portion of said movable platform has an outer level.

32. The therapeutic measuring device of claim 31, wherein said outer level of said stationary portion of said movable platform is disposed where said top side of said stationary portion of said movable platform meets said outer side of said stationary portion of said movable platform, midway therealong.

33. The therapeutic measuring device of claim 26, wherein said stationary portion of said movable platform has an inner level.

34. The therapeutic measuring device of claim 33, wherein said inner level of said stationary portion of said movable platform is disposed where said top side of said stationary portion of said movable platform meets said inner side of said stationary portion of said movable platform, midway therealong.

35. The therapeutic measuring device of claim 26, wherein said stationary portion of said movable platform has a bottom side.

36. The therapeutic measuring device of claim 35, wherein said stationary portion of said movable platform contains a screw jack assembly.

37. The therapeutic measuring device of claim 36, wherein said top side of said stationary portion of said movable platform contains a trough.

38. The therapeutic measuring device of claim 37, wherein said trough of said stationary portion of said movable platform receives said movable portion of said movable platform so as to allow said movable portion of said movable platform to move only directly vertically without twisting in said trough of said stationary portion of said movable platform for maintaining said movable part of said movable portion level.

39. The therapeutic measuring device of claim 37, wherein said trough of said stationary portion of said movable platform has a top side.

40. The therapeutic measuring device of claim 39, wherein said top side of said trough of said stationary portion of said movable platform is open.

41. The therapeutic measuring device of claim 37, wherein said trough of said stationary portion of said movable platform is parallelepiped-shaped.

42. The therapeutic measuring device of claim 37, wherein said trough of said stationary portion of said movable platform has an inner side.

43. The therapeutic measuring device of claim 42, wherein said inner side of said trough of said stationary portion of said movable platform is parallel to said inner side of said stationary portion of said movable platform.

44. The therapeutic measuring device of claim 42, wherein said inner side of said trough of said stationary portion of said movable platform is inward of said inner side of said stationary portion of said movable platform.

45. The therapeutic measuring device of claim 37, wherein said trough of said stationary portion of said movable platform has a front side.

46. The therapeutic measuring device of claim 45, wherein said front side of said trough of said stationary portion of said movable platform is parallel to said front side of said stationary portion of said movable platform.

47. The therapeutic measuring device of claim 45, wherein said front side of said trough of said stationary portion of said movable platform is inward of said front side of said stationary portion of said movable platform.

48. The therapeutic measuring device of claim 45, wherein said trough of said stationary portion of said movable platform has a rear side.

49. The therapeutic measuring device of claim 48, wherein said rear side of said trough of said stationary portion of said movable platform is parallel to said rear side of said stationary portion of said movable platform.

50. The therapeutic measuring device of claim 48, wherein said rear side of said trough of said stationary portion of said movable platform is inward of said rear side of said stationary portion of said movable platform.

51. The therapeutic measuring device of claim 37, wherein said trough of said stationary portion of said movable platform has a height.

52. The therapeutic measuring device of claim 37, wherein said trough of said stationary portion of said movable platform has an outer side.

53. The therapeutic measuring device of claim 52, wherein said outer side of said trough of said stationary portion of said movable platform is parallel to said outer side of said stationary portion of said movable platform.

54. The therapeutic measuring device of claim 52, wherein said outer side of said trough of said stationary portion of said movable platform is inward of said outer side of said stationary portion of said movable platform.

55. The therapeutic measuring device of claim 52, wherein said trough of said stationary portion of said movable platform has a bottom side.

56. The therapeutic measuring device of claim 55, wherein said bottom side of said trough of said stationary portion of said movable platform is parallel to said bottom side of said stationary portion of said movable platform.

57. The therapeutic measuring device of claim 55, wherein said bottom side of said trough of said stationary portion of said movable platform is upwards of said bottom side of said stationary portion of said movable platform.

58. The therapeutic measuring device of claim 55, wherein said movable portion of said movable platform has an outer side.

59. The therapeutic measuring device of claim 58, wherein said movable portion of said movable platform has an inner side.

60. The therapeutic measuring device of claim 59, wherein said movable portion of said movable platform has a front side.

61. The therapeutic measuring device of claim 60, wherein said front side of said movable portion of said movable platform is parallel to said front side of said stationary portion of said movable platform.

62. The therapeutic measuring device of claim 60, wherein said front side of said movable portion of said movable platform is inward of said front side of said stationary portion of said movable platform.

63. The therapeutic measuring device of claim 60, wherein said front side of said movable portion of said movable platform is substantially coplanar with said front side of said trough of said stationary portion of said movable platform.

64. The therapeutic measuring device of claim 60, wherein said movable portion of said movable platform has a rear side.

65. The therapeutic measuring device of claim 64, wherein said rear side of said movable portion of said movable platform is parallel to said rear side of said stationary portion of said movable platform.

66. The therapeutic measuring device of claim 64, wherein said rear side of said movable portion of said movable platform is inward of said rear side of said stationary portion of said movable platform.

67. The therapeutic measuring device of claim 64, wherein said rear side of said movable portion of said movable platform is substantially coplanar with said rear side of said trough of said stationary portion of said movable.

68. The therapeutic measuring device of claim 64, wherein said movable portion of said movable platform has a top side.

69. The therapeutic measuring device of claim 68, wherein said movable portion of said movable platform has a front level.

70. The therapeutic measuring device of claim 69, wherein said front level of said movable portion of said movable platform is disposed where said top side of said movable portion of said movable platform meets said front side of said movable portion of said movable platform, midway therealong.

71. The therapeutic measuring device of claim 68, wherein said movable portion of said movable platform has a rear level.

72. The therapeutic measuring device of claim 71, wherein said rear level of said movable portion of said movable platform is disposed where said top side of said movable portion of said movable platform meets said rear side of said movable portion of said movable platform, midway therealong.

73. The therapeutic measuring device of claim 68, wherein said movable portion of said movable platform has an outer level.

74. The therapeutic measuring device of claim 73, wherein said outer level of said movable portion of said movable platform is disposed where said top side of said movable portion of said movable platform meets said outer side of said movable portion of said movable platform, midway therealong.

75. The therapeutic measuring device of claim 68, wherein said movable portion of said movable platform has an inner level.

76. The therapeutic measuring device of claim 75, wherein said inner level of said movable portion of said movable platform is disposed where said top side of said movable portion of said movable platform meets said inner side of said movable portion of said movable platform, midway therealong.

77. The therapeutic measuring device of claim 58, wherein said movable portion of said movable platform has a bottom side.

78. The therapeutic measuring device of claim 58, wherein said outer side of said movable portion of said movable platform is parallel to said outer side of said stationary portion of said movable platform.

79. The therapeutic measuring device of claim 58, wherein said outer side of said movable portion of said movable platform is inward of said outer side of said stationary portion of said movable platform.

80. The therapeutic measuring device of claim 58, wherein said outer side of said movable portion of said movable platform is substantially coplanar with said outer side of said trough of said stationary portion of said movable platform.

81. The therapeutic measuring device of claim 77, wherein said bottom side of said movable portion of said movable platform is parallel to said bottom side of said stationary portion of said movable platform.

82. The therapeutic measuring device of claim 77, wherein said bottom side of said movable portion of said movable platform is upwards of said bottom side of said stationary portion of said movable platform.

83. The therapeutic measuring device of claim 77, wherein said outer side of said movable portion of said movable platform has a measuring scale therealong for viewing.

84. The therapeutic measuring device of claim 83, wherein said measuring scale of said outer side of said movable portion of said movable platform determines how far said movable portion of said movable platform moves with respect to said stationary portion of said movable platform, which in turn is for indicating the difference in length between the pair of legs of the user.

85. The therapeutic measuring device of claim 83, wherein said screw jack assembly has a vertical portion.

86. The therapeutic measuring device of claim 85, wherein said screw jack assembly has a horizontal portion.

87. The therapeutic measuring device of claim 86, wherein said horizontal portion of said screw jack assembly extends operatively from said vertical portion of said screw jack assembly, through said stationary portion of said movable platform, and terminates at said front side of said stationary portion of said movable platform as a bore.

88. The therapeutic measuring device of claim 87, wherein said bore of said horizontal portion of said screw jack assembly is for receiving an Allen key, which when rotated, rotates said horizontal portion of said screw jack assembly, which in turn rotates said vertical portion of said screw jack assembly, causing said movable portion of said movable platform to raise revealing a point on said measuring scale of said outer side of said movable portion of said movable platform and thereby disclosing the difference in length of the pair of legs of the user.

89. The therapeutic measuring device of claim 85, wherein said vertical portion of said screw jack assembly extends upwardly from said bottom side of said trough of said stationary portion of said movable platform to said bottom side of said movable portion of said movable platform, at the center of gravity of said movable portion of said movable platform.

90. The therapeutic measuring device of claim 85, wherein said vertical portion of said screw jack assembly extends centrally from said bottom side of said trough of said stationary portion of said movable platform.

91. The therapeutic measuring device of claim 17, wherein said height of said stationary portion of said movable platform is equal to said height of said stationary platform when both are placed upon a level support surface.

* * * * *